(12) United States Patent
Oishi et al.

(10) Patent No.: US 7,678,082 B2
(45) Date of Patent: Mar. 16, 2010

(54) ESOPHAGUS STOMA BUTTON

(75) Inventors: Hideto Oishi, 601 Nogata Matuyama Hights, 7-5, Maruyama 2-chome, Nakano-ku, Tokyo 165-0021 (JP); Masato Nakagawa, Akita (JP); Yukihiko Sakaguchi, Akita (JP)

(73) Assignees: Sumitomo Bakelite Co., Ltd., Tokyo (JP); Hideto Oishi, Tokyo (JP)

( * ) Notice: Subject to any disclaimer, the term of this patent is extended or adjusted under 35 U.S.C. 154(b) by 98 days.

(21) Appl. No.: 10/491,190

(22) PCT Filed: Oct. 3, 2001

(86) PCT No.: PCT/JP01/08709

§ 371 (c)(1),
(2), (4) Date: Sep. 20, 2004

(87) PCT Pub. No.: WO03/030983

PCT Pub. Date: Apr. 17, 2003

(65) Prior Publication Data

US 2005/0033240 A1    Feb. 10, 2005

(51) Int. Cl.
*A61M 5/32* (2006.01)
(52) U.S. Cl. ............. 604/174; 604/164.01; 604/164.02; 604/164.03; 604/103; 604/104; 604/270; 604/264; 604/178; 604/179; 604/533
(58) Field of Classification Search .............. 604/93.01, 604/77, 103.03, 158, 890.1, 96.01, 97.01, 604/164.01–164.03, 103–104, 270, 264, 604/174–175, 178–179, 275, 533
See application file for complete search history.

(56) References Cited

U.S. PATENT DOCUMENTS

| 3,973,569 | A | * | 8/1976 | Sheridan et al. | ........ 128/207.15 |
| 4,315,513 | A | * | 2/1982 | Nawash et al. | .............. 604/537 |
| 4,685,901 | A | | 8/1987 | Parks | |
| 4,735,334 | A | * | 4/1988 | Abbott | ........................ 222/546 |
| 4,863,438 | A | * | 9/1989 | Gauderer et al. | ............. 604/247 |

(Continued)

FOREIGN PATENT DOCUMENTS

JP    63-130073 A    6/1988

(Continued)

*Primary Examiner*—Nicholas D Lucchesi
*Assistant Examiner*—Quynh-Nhu H Vu
(74) *Attorney, Agent, or Firm*—Westerman, Hattori, Daniels & Adrian, LLP (57) ABSTRACT

The purpose of this invention is to provide an esophagus stoma button capable of safely forming and maintaining a stoma hole provided in an esophagus and reducing the discomfortableness of a patient. To achieve the object, in the present invention, the stoma button 9 is comprised of a shaft part 1 and a flange part 2 provide at the rear end of the shaft part rounded at the tip thereof. More specifically, in the esophagus stoma button 9, a flange part is provide at the rear end of the shaft part rounded at the tip thereof, and a lumen having a generally circular cross section in the area ranging from the shaft part to the flange part is provided, a means for fixing a catheter for infusion is provided in the flange part with a flat and generally circular shape and a means for tightly closing the opening of the flange part is provided at the opening thereof.

16 Claims, 9 Drawing Sheets

U.S. PATENT DOCUMENTS

| | | | |
|---|---|---|---|
| 4,944,732 A * | 7/1990 | Russo | 604/247 |
| 5,125,897 A * | 6/1992 | Quinn et al. | 604/99.03 |
| 5,133,470 A * | 7/1992 | Abrams et al. | 215/250 |
| 5,267,968 A | 12/1993 | Russo | |
| 5,318,525 A * | 6/1994 | West et al. | 604/95.04 |
| 5,336,203 A * | 8/1994 | Goldhardt et al. | 604/247 |
| 5,352,198 A * | 10/1994 | Goldenberg et al. | 604/95.04 |
| 5,356,017 A * | 10/1994 | Rohr et al. | 215/216 |
| 5,358,488 A * | 10/1994 | Suriyapa | 604/103.03 |
| 5,364,367 A * | 11/1994 | Banks et al. | 604/174 |
| 5,368,556 A * | 11/1994 | Lecuyer | 604/8 |
| 5,383,896 A * | 1/1995 | Gershony et al. | 606/213 |
| 5,395,015 A * | 3/1995 | Bolen et al. | 222/546 |
| 5,397,013 A * | 3/1995 | Adams et al. | 220/255.1 |
| 5,423,442 A * | 6/1995 | Nozawa et al. | 215/235 |
| 5,484,420 A * | 1/1996 | Russo | 604/178 |
| 5,549,657 A * | 8/1996 | Stern et al. | 604/537 |
| 5,556,385 A * | 9/1996 | Andersen | 604/174 |
| 5,569,206 A * | 10/1996 | Gorman et al. | 604/167.01 |
| 5,766,249 A * | 6/1998 | Griffith | 600/30 |
| 5,799,840 A * | 9/1998 | Mogard | 222/541.5 |
| 5,820,606 A * | 10/1998 | Davis et al. | 604/256 |
| 5,832,971 A * | 11/1998 | Yale et al. | 141/329 |
| 6,039,714 A * | 3/2000 | Cracauer et al. | 604/174 |
| 6,045,536 A * | 4/2000 | Meier et al. | 604/174 |
| 6,231,549 B1 * | 5/2001 | Noecker et al. | 604/175 |
| 6,289,906 B1 * | 9/2001 | Vanden Dries et al. | 134/117 |
| 6,328,720 B1 * | 12/2001 | McNally et al. | 604/332 |
| 6,382,476 B1 * | 5/2002 | Randall et al. | 222/545 |
| 6,402,722 B1 * | 6/2002 | Snow et al. | 604/164.05 |
| 6,419,670 B1 * | 7/2002 | Dikeman | 604/533 |

FOREIGN PATENT DOCUMENTS

| | | |
|---|---|---|
| JP | 04-42839 A | 2/1992 |
| JP | 11-309215 A | 9/1999 |

* cited by examiner

FIG. 18

ESOPHAGUS STOMA BUTTON

TECHNICAL FIELD

The present invention relates to a medical tool for reliably securing a route for discharging bodily fluid and infusing chemical liquid or eutrophic or the like with safety, and more particularly, to an esophagus stoma button capable of forming and maintaining a stoma formed in an esophagus.

BACKGROUND OF THE INVENTION

Conventionally, especially as a method for giving nutrition through an intestine, endoscopic stomach stoma through skin (PEG) which is one of endoscopic operations for forming a stoma in skin surfaces of stomach lumen and abdominal wall using an endoscope was developed by Gaudert (pediatric surgeon) and Ponsky (endoscopic surgeon) in 1979 (Japanese Patent Application Laid-open No. H6-503243), and some techniques using this have been developed and have become widespread. However, since a stomach lining or an abdominal wall is subjected to centesis, this operation can not be used or it is difficult to use this operation "in a case in which a large amount of ascites is stored", "in a case in which a liver or a transverse colon exists between a stomach and an abdominal wall", and "a case in which the patient has anamnesis of stomach operation.

There is a method for indwelling a tube in a stomach through a nose, but when the tube is allowed to stay in the stomach for a long term, a pain in a nostril, a nasal vacity or a pharynx becomes strong, an ulcer is formed in the nostril and it becomes difficult to keep allowing the tube to stay in the stomach in some cases, and pneumonia is supervened because it is difficult to discharge sputum in some cases. These are not preferable in terms of QOL.

The present inventors proposed an invention of a medical tube inserting tool and a method for using this tool in Japanese Patent Application Laid-open No. H10-17994. In this invention, in order to overcome the inconvenience of the PEG and the tube through nose, a route for discharging bodily fluid and infusing chemical liquid and eutrophic through esophageal is reliably secured with safety. In this invention, however, there is no detail description concerning the tube to be stayed, and since it is necessary to use a long tube when a currently widely used tube is used, a portion of the tube projecting from a body becomes long, this portion is burdensome for a patient who needs the tube in his or her body for a long term. Therefore, there is a possibility that the patient himself or herself intentionally pull out the tube in some cases.

As a method for overcoming the inconvenience caused because the portion of the tube projecting from the body becomes long, there is proposed a medical tool comprising a mushroom-like or semi-spherical member to be fixed in a body. In this medical tool, the projecting portion is reduced in size (U.S. Pat. Nos. 5,549,657, and 4,863,438). When this proposed tool is allowed to stay in the esophagus, however, there is a problem that the fixed portion becomes bulky at the entrance portion of the esophagus, and it becomes difficult to take nutrition through a mouth.

On the other hand, when the tube is allowed to stay for a long term, in order to avoid an excessive burden on a body, it is effective to use a soft material on a shaft portion, but since the tube is inserted directly through the stoma when the tube is exchanged, appropriate hardness is also required. A cervix structure and the formation angle of a stoma are different depending upon patients, and if an angle formed by a shaft part and a flange part is fixed, a burden is put on a body in some cases. When a catheter for transfusion is to be connected, it is necessary to ensure the air-tightness of the connection and reliable fixed state. Some patients repeat vomiting after eutrophic is infused into a stomach. For such patient, it is necessary to insert a tip of the shaft part to a small intesine. There are problems that this inserting operation is not easy, it takes time to allow the tube to stay in the stomach, and burdens are put on an operator and a patient mentally and physically.

The present invention has been accomplished in view of the above circumstances, and it is an object of the invention to provide a medical tool for reliably securing a route for discharging bodily fluid and infusing chemical liquid or eutrophic or the like with safety, and more particularly, to provide an esophagus stoma button capable of forming and maintaining a stoma formed in an esophagus with safety which reduces the annoyance of a patient.

DISCLOSURE OF THE INVENTION

That is, the present invention of an esophagus stoma button wherein a flange part is provided at the rear end of a shaft part rounded at the tip thereof.

According to a more concrete configuration of the present invention, the esophagus stoma button is comprised of a flange part provided at the rear end of a shaft part rounded at the tip thereof, a lumen having a generally circular cross section in the area ranging from the shaft part to the flange part, a means for fixing a catheter for transfusion provided in the flange part of flat and generally circular shape and a means for tightly closing the opening of the flange part provided therein.

According to another concrete configuration of the invention, the esophagus stoma button is comprised of a flange part provided at the rear end of a shaft part rounded at the tip thereof, a lumen having a generally circular cross section in the area ranging from the shaft part to the flange part, a means for fixing a catheter for transfusion provided in the flange part of flat and generally circular shape, a means for tightly closing the opening of the flange part provided therein, and a check valve provided in the vicinity of the opening of the flange part.

BEST MODE FOR CARRYING OUT THE INVENTION

Figure 1:
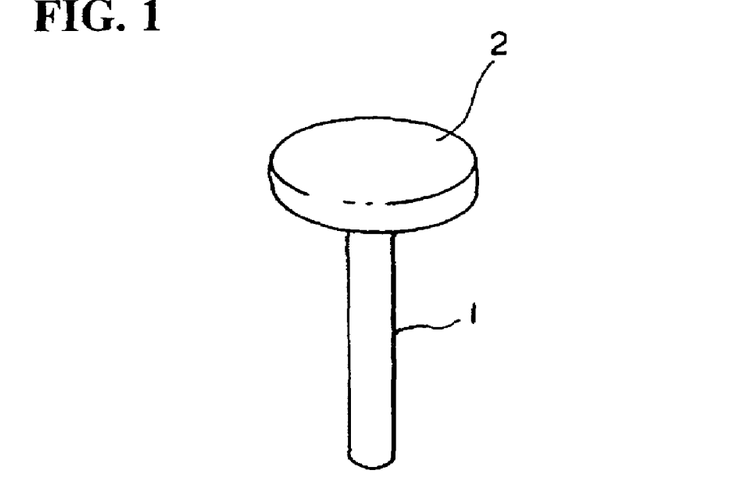
FIG. 1 is a perspective view of an esophagus stoma button of a first embodiment of the present invention.

As shown in FIG. 1, an esophagus stoma button of a first embodiment of the present invention is comprised of a shaft part (1) and a substantially disc-like flange part (2) provided on the rear end (upper end in FIG. 1) of the shaft portion (1). The shaft portion (1) is cylindrical in shape, and its tip (lower end in FIG. 1) is rounded to prevent a mucous membrane of an esophagus from being damaged. It is preferable that the shaft portion (1) has a length suitable for the physical constitution of a patient so that the tip of the shaft portion (1) is reliably located in the esophagus, and its thickness is equal to that of a catheter which infuses eutrophic or chemical liquid so that a stoma is maintained and the button and the catheter can easily be pulled in and out. The shaft part (1) has appropriate softness and resilience at the normal room temperature and body heat, and preferable materials of the shaft part (1) are synthetic resin such as soft vinyl chloride resin, polyurethane resin, polyamide resin, elastomer thereof, silicone rubber, but the material is not limited to them. The shaft part (1) may have properties for maintaining its shape so that a position of the shaft part (1) in the body can be known.

Figure 2:
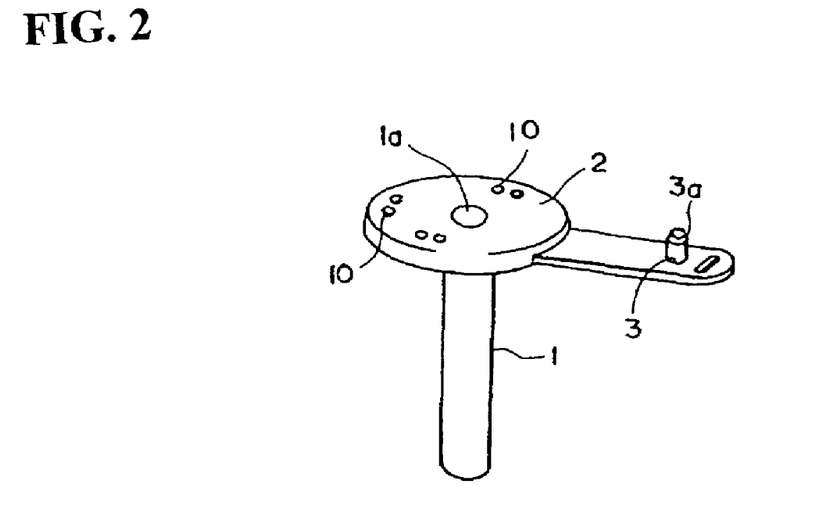
FIG. 2 is a perspective view of a esophagus stoma button of a second embodiment of the invention.

FIG. 2 shows an esophagus stoma button of a second embodiment of the invention. The esophagus stoma button is comprised of the shaft part (1), the flange part (2) and a cap part (3). In the example in FIG. 2, the shaft part (1) is cylindrical in shape, and is formed with a lumen (1*a*) formed through its rear end to tip through which a guide wire or transfusion tube is inserted. Like the example shown in FIG. 1, it is desirable that the shaft part (1) has a length suitable for the physical constitution of a patient, and has such a thickness that a tube to be inserted into the esophagus stoma button can easily be pulled in and out.

Figure 12:
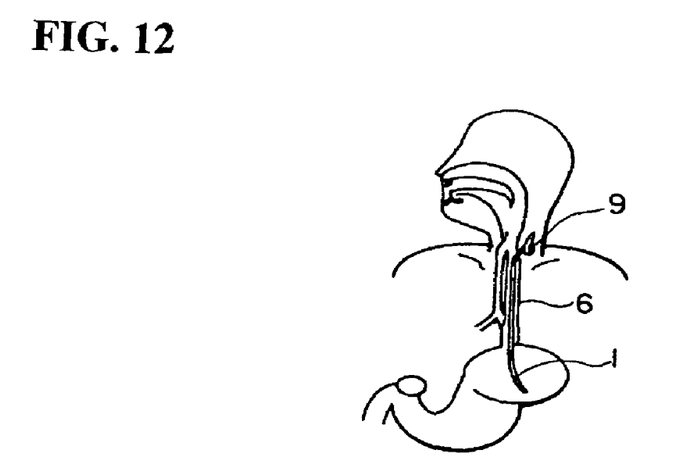
FIG. 12 is a schematic view showing the indwelling state of the esophagus stoma button of the invention.

In the case of the embodiment shown in FIG. 2, the eutrophic or chemical liquid can be infused directly into a stomach (or intestine). In such a case, as shown in FIG. 12, it is necessary to allow the tip of the shaft portion (1) to stay in an appropriate position in the stomach (or intestine). For this reason, the length of the shaft part (1) is previously set to a length from a fistula to a stomach (or intestine), or the shaft part (1) is allowed to stay in a predetermined position and then, the shaft part (1) is cut into a desired length, and the flange part (2) is fitted over the rear end of the shaft portion (1). This shaft part (1) also has appropriate softness and resilience at the normal room temperature and body heat, and preferable materials of the shaft part (1) are synthetic resin such as soft vinyl chloride resin, polyurethane resin, polyamide resin, elastomer thereof, silicone rubber, but the material is not limited to them. When the transfusion tube or the guide wire is inserted or pulled out, in order to suppress the resistance, a forming material into which lubricant such as silicone oil is impregnated may be used, or an inner surface of the shaft part (1) may be subjected to a hydrophilic procedure.

The flange part (2) in the above-described esophagus stoma buttons needs to have appropriate softness since the flange part (2) comes into contact directly with a skin. The flange part (2) also needs appropriate hardness for preventing the shaft portion (1) from being pulled into a body due to shrinking motion of the esophagus or stomach (or intestine). Thus, preferable forming materials of the flange part (2) are soft vinyl chloride resin, polyurethane resin, polyamide resin, elastomer thereof and silicone rubber. If the size and thickness of the material are appropriately set, excellent softness and hardness can be obtained.

Figure 14:
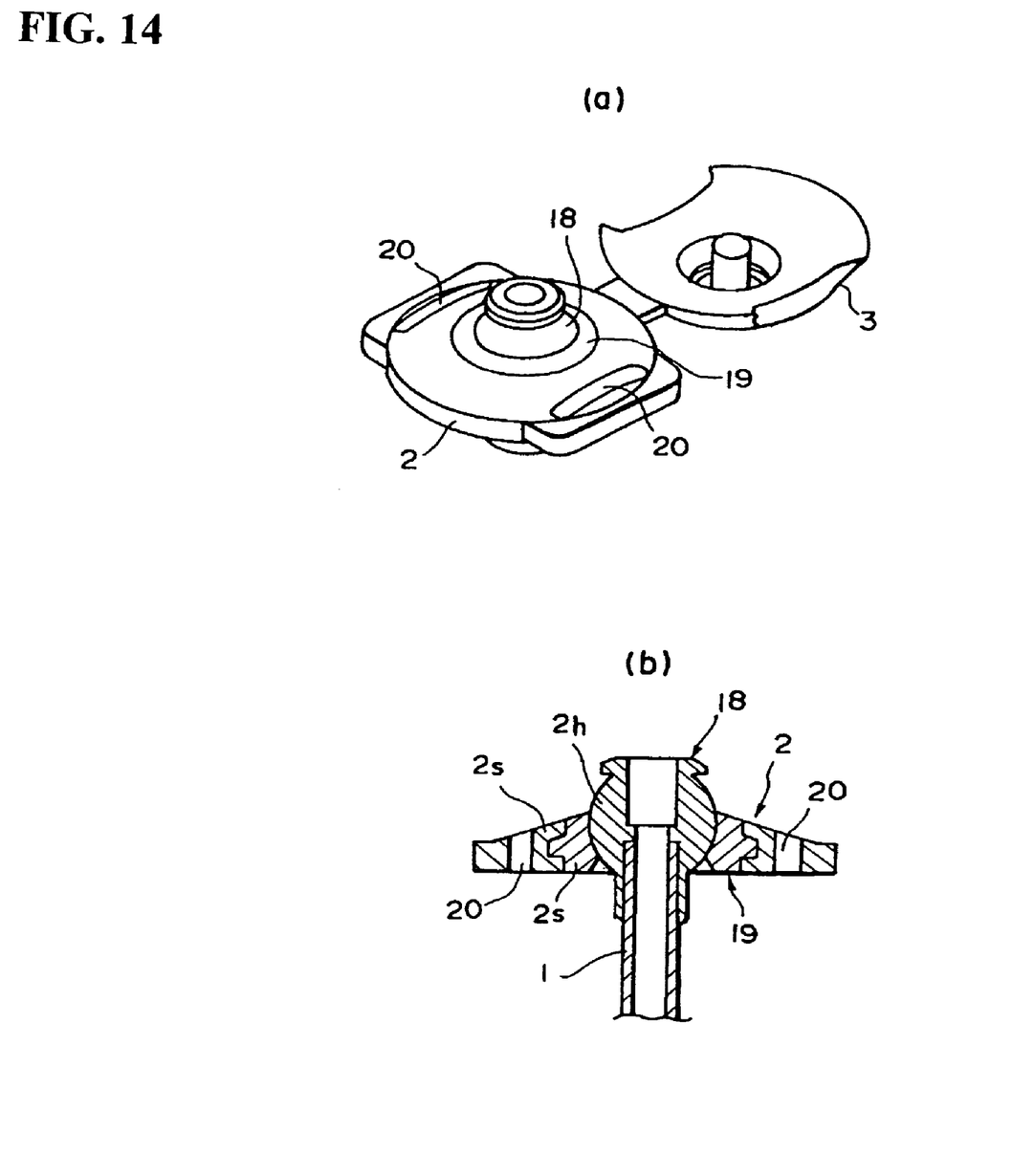
Figure 15:
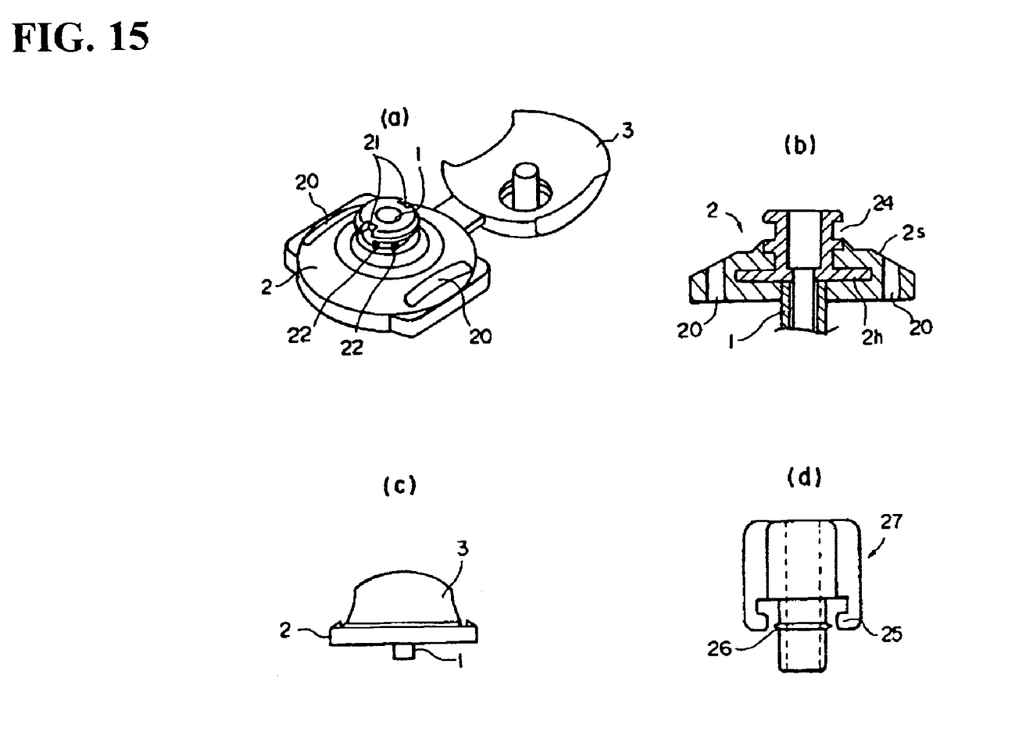

Concerning the above points, as in embodiments shown in FIGS. 14(*b*) and 15(*b*), if an inner hard material (2*h*) is integrally covered with soft material (2*s*) to form the flange part (2), the same effect can be obtained. In this case, since chemical liquid or eutrophic comes into contact with the hard material, the material which is resistant to chemicals and eutrophic (e.g., fatty emulsion) is required. Preferable materials thereof are polyethylene resin, polypropylene resin, polyvinyl chloride resin, polyurethane resin, polyamide resin, polyether sulfone resin. Since the soft material (2*s*) needs appropriate softness as described above, preferable materials thereof are soft vinyl chloride resin, polyurethane resin, polyamide resin or elastomer thereof, or silicone rubber.

Figure 4:
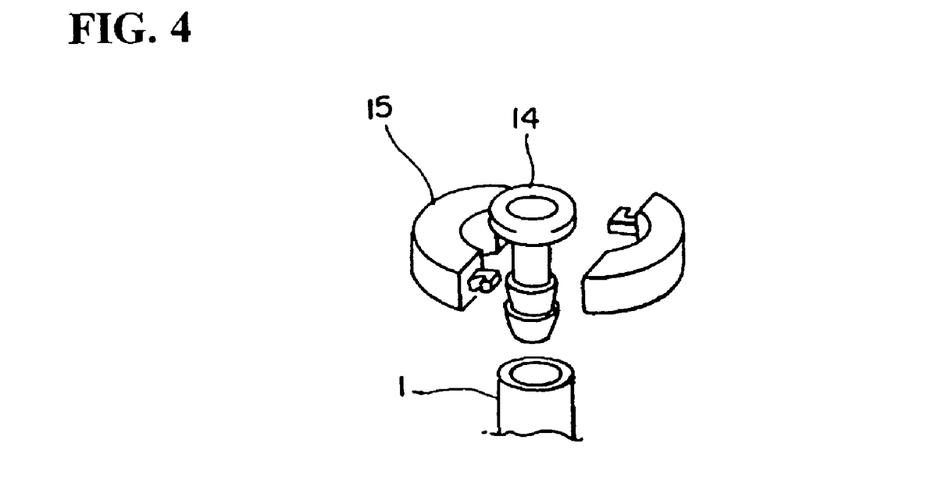
FIG. 4 is a schematic perspective view showing a structure of a flange part of a fourth embodiment of the esophagus stoma button of the invention.

In this invention, the shaft part (1) and the flange part (2) are connected to each other by integral forming, adhesive or fitting. In an esophagus stoma button (9) of the invention employing a using mode shown in FIG. 12, when the flange part (2) is retrofitted to the shaft part (1) in order to prevent the shaft portion (1) from being pulled into a body due to the shrinking motion of the esophagus or stomach (or intestine), it is necessary to reliably fix the shaft part (1) and a connector (14) by a split type fixing flange (15) after the connector (14) is inserted into the rear end of the shaft portion (1) as shown in FIG. 4. In this case, since the soft shaft part (1) is sandwiched and fixed between the connector (14) and the fixing flange (15), it is preferable to use-hard materials for the connector (14) and the fixing flange (15), and examples of the preferable material are polyvinyl chloride resin, polysulfone resin, acrylic resin, ABS resin, polymethyl pentene resin, polyamide resin, polyurethane resin, polyester resin or polymer alloy thereof.

Figure 3:
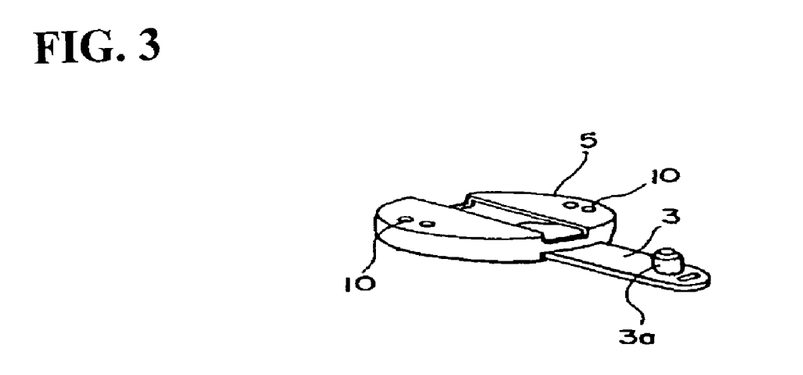
FIG. 3 is a perspective view of one example of a cap portion in a third embodiment of the esophagus stoma button of the invention.

In the case of the esophagus stoma button of this invention having the lumen (1*a*), the flange portion (2) is provided with a cap portion (3) for keeping the air-tightness. The cap portion (3) may be integrally formed on the flange part (2), or the cap portion (3) may be integrally formed on a cover (5) which covers the flange part (2) as shown in FIG. 3. The shape of the cap portion (3) is not especially limited, but in order to prevent a patient from unintentionally opening the cap portion (3), it is preferable form the cap portion (3) into a curved surface such as substantially domical shape as shown in FIG. 15(c) so that the finger or the nail of the patient can not easily catch. The esophagus stoma button (9) of the invention in the indwelling mode as shown in FIG. 12 is fixed to a patient by one needle suture in some cases. Therefore, as shown in FIGS. 2 and 3, the flange part (2) or the cover (5) may be provided at its outer periphery with a necessary number of small holes (10). Further, as shown in FIGS. 14(a), 14(b), 15(a) and 15(b), a slit (20) may be provided so that the esophagus stoma button can be fixed by a wide band instead of fixing by means of suture.

Figure 5:
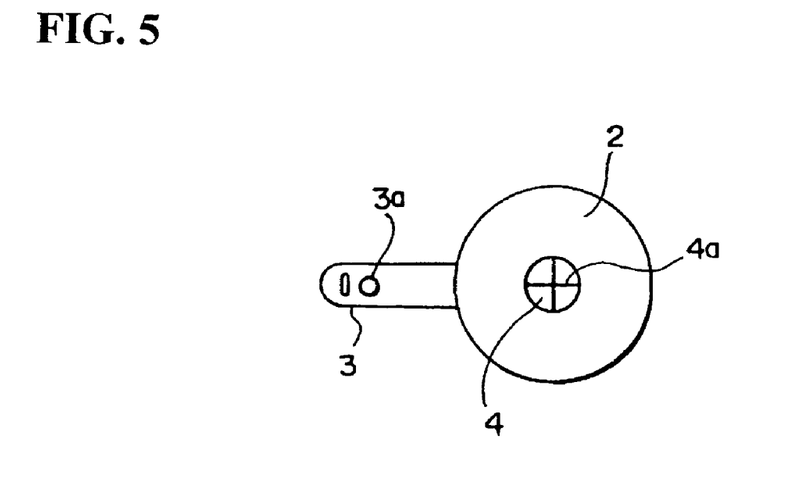
FIG. 5 is a planar view of an esophagus stoma button of a fifth embodiment of the invention.
Figure 6:
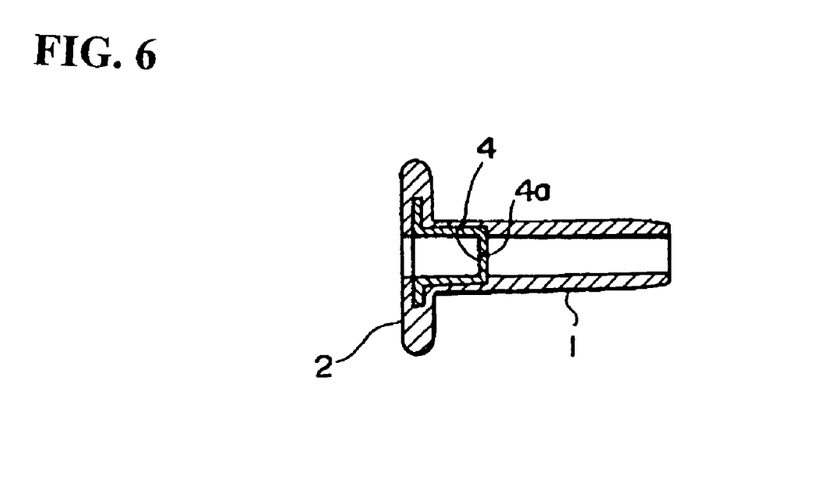
FIG. 6 is a sectional view of the esophagus stoma button shown in FIG. 5.
Figure 7:
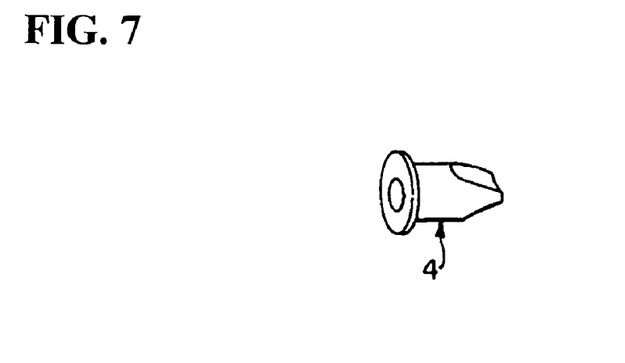
FIG. 7 is a perspective view showing another example of a check valve.

Next, a check valve (4) shown in FIG. 6 provided in the vicinity of the flange part (2) will be explained. This check valve (4) is provided to prevent contents in a body from leaking out. Its shape, structure and material are not especially limited, but it is necessary that a tube can smoothly be pulled in and out, the air-tightness when the tube is not yet inserted can be secured and the check valve (4) is not bulky. Therefore, in this invention, it is preferable that the check valve (4) has an elastic flat-plate like structure having a cross incision (4a) as shown in FIGS. 5 and 6, or that the check valve (4) is of a duck bill type. Preferable examples of the forming material of the check valve (4) are thermoplastic elastomer, silicone rubber and the like.

The esophagus stoma button of this invention is allowed to stay in accordance with a state of a cervix of a patient. Thus, it is preferable that bulk of the esophagus stoma button can be suppressed and an angle which is formed by the shaft portion (1) and the flange portion (2) can be changed. FIG. 14(b) shows such an example. In this example, the shaft part (1) is provided at its rear end with a movable connector (18) having a convex sphere, the flange part (2) is provided with a holder (19) having a concave sphere so that the shaft part (1) and the flange part (2) can be held by each other at a predetermined angle in any direction. In this case, since the holder (19) comes into contact with a skin, it is preferable that the holder (19) is covered with soft material.

As in the example of allowing the esophagus stoma button to stay in the body as shown in FIG. 12, if the tip of the shaft portion (1) is located in a stomach (or intestine), a transfusion catheter is connected directly to the flange part (2) of the esophagus stoma button (9) when chemical liquid or eutrophic is to be infused. In order to prevent the catheter from being pulled out, a means for reliably fixing the flange part (2) and the catheter to each other is required. Although the catheter is not limited to such a structure, a tube connector (27) having a structure shown in in FIG. 15(b) is used as one example. In this connector (27), a retaining hook (25) formed around an outer periphery of its body is inserted into a notch (21) formed in an upper end of the shaft part (1) and then, the connector (27) is rotated along a groove (24), the hook (25) rides over a small projection (22), the connector (27) is rotated through a predetermined angle until its rotation is stopped by a small projection (23), thereby fixing the connection tube to the esophagus stoma button. A force is applied to this tube connector (27) in the rotational direction when the tube is connected, but the force at the time of connection of the tube is not applied in a direction in which the stoma is pushed and thus, the QOL can further be enhanced. If the connector (27) is provided at its lower connecting portion with a seal ring (26), the air-tightness can be maintained.

Figure 16:
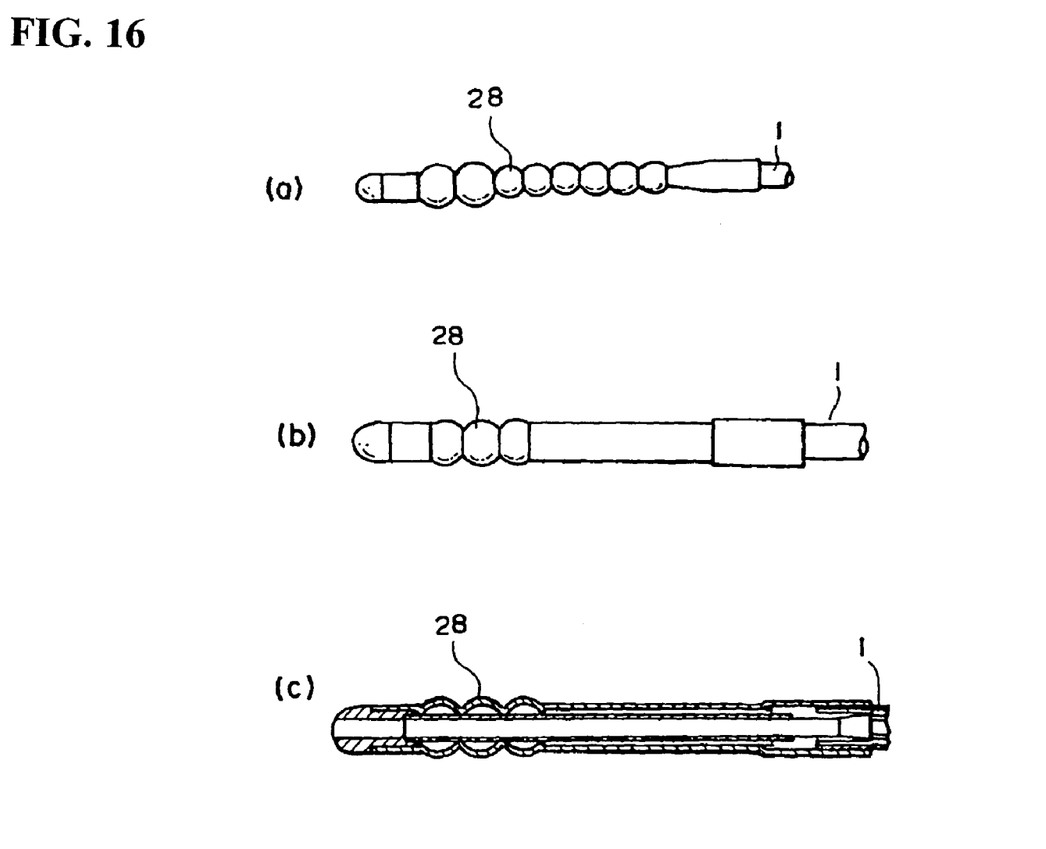

When the tip end of the shaft part (1) of the esophagus stoma button of this invention is allowed to stay in a stomach or a small intestine, as shown in FIGS. 16(a) to (c), if the shaft is provided at its tip with a weight (28), the inserting properties can be enhanced. A shape and material of the weight (28) are not limited, but as shown in FIGS. 16(a) to (c), it is possible to preferably use a plurality of metal or ceramic spherical or cylindrical weights (28) as used in a general ileus tube, a spherical cylindrical weight (28) which is provided with a small hole such as to penetrate a central portion of the weight (28) and which is covered with a soft tube, or a spherical cylindrical weight (28) which is provided with a small hole such as to penetrate a central portion of the weight (28) and which is inserted into a tube or a spring and covered with a soft tube.

Figure 13:
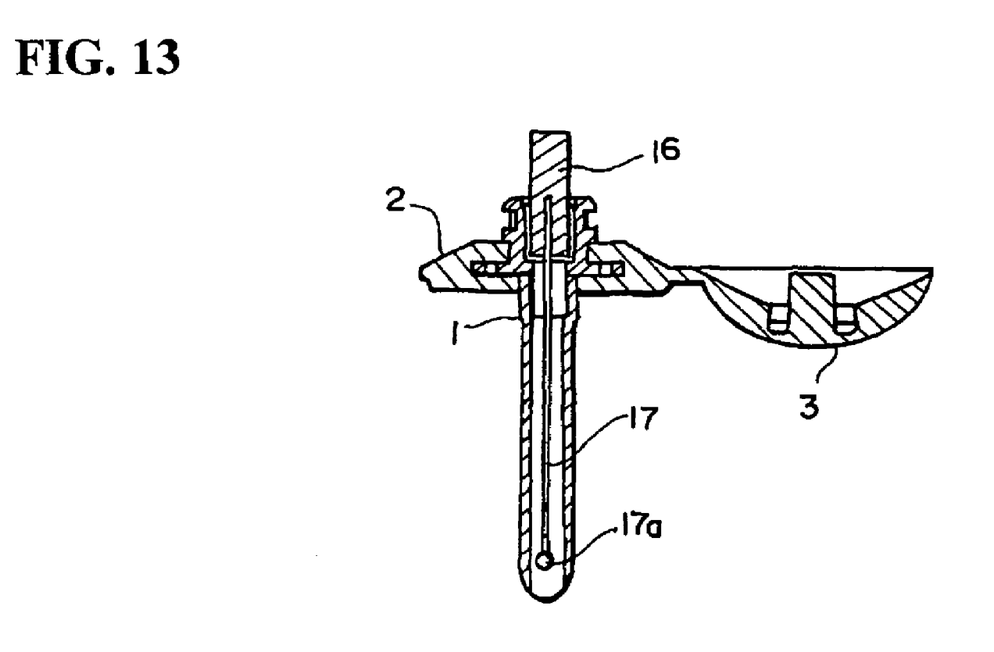
FIG. 13 is a sectional view showing one example of an attachable and detachable stylet applied to the esophagus stoma button of the invention and its inserted state, FIG. 14 show an esophagus stoma button of a sixth embodiment of the invention wherein FIG. 14(*a*) is a perspective view thereof and FIG. 14(*b*) is a partial vertical sectional view of FIG. 14(*a*), FIG. 15 show a flange part of an esophagus stoma button of a seventh embodiment of the invention wherein FIG. 15(*a*) is a perspective view thereof, FIG. 15(*b*) is a partial vertical sectional view of FIG. 15(*a*), FIG. 15(*c*) is a front view showing a state in which a cap is fastened, and FIG. 15(*d*) is a front view showing one example of a connection tube connector applied to the flange portion of FIG. 15(*a*), FIG. 16 are schematic side views showing the tip of a shaft portion in an eighth embodiment of the esophagus stoma button of the invention wherein FIG. 16(*a*) is a schematic view showing a first embodiment of a weight added on the tip of a shaft, FIG. 16(*b*) is a schematic view showing a second embodiment of the weight added on the tip of the shaft and FIG. 16(*c*) is a sectional view of FIG. 16(*b*)

In the esophagus stoma button of this invention, a material having softness as high as possible is used for the shaft part (1) which stays in a body, and the esophagus stoma button may be provided with an attachable and detachable wire or the like so that the inserting properties are not deteriorated. A shape, a structure and a material of the wire are not especially limited, but as shown in FIG. 13 for example, a preferable wire has a fixing tool (16) for fitting a metal stylet (17) provided at its tip with a fine ball (17a) into the flange part (2).

Figure 17:
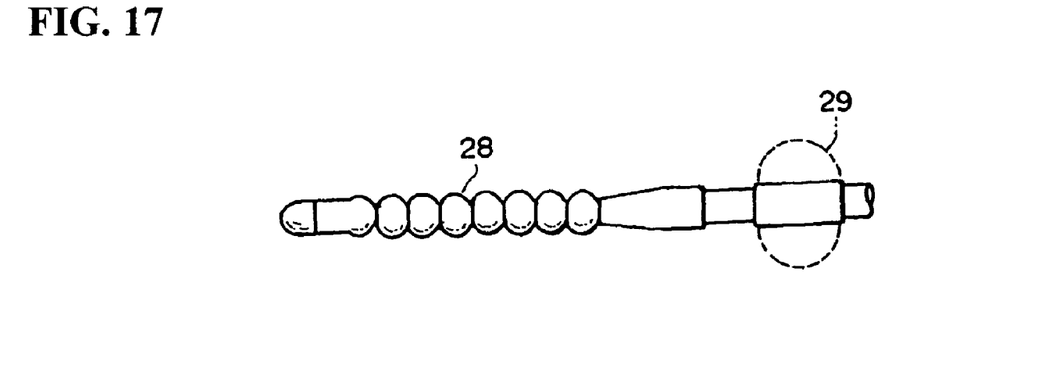
FIG. 17 is a schematic side view showing the tip of a shaft part in a ninth embodiment of the esophagus stoma button of the invention.

In the esophagus stoma button of the invention, when the tip of the shaft part (1) is allowed to stay in a small intestine, if the tip is provided with a balloon (29) as shown in FIG. 17, the inserting properties can further be enhanced. The balloon (29) is expanded and shrunk for confirmation and then, the balloon (29) is inserted into a body. When the balloon (29) is inserted through a sheath tube, if the balloon is not reliably shrunk due to a wrinkle formed after the shrinkage, the catheter can not be inserted into the sheath. Therefore, a material having excellent shrinking properties, and silicone rubber, natural rubber, isoprene rubber and the like are used.

Figure 18:
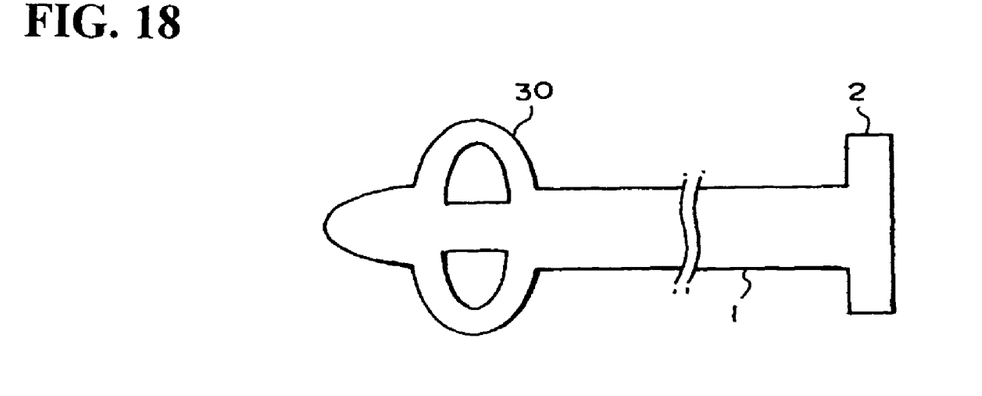
FIG. 18 is a schematic side view showing an esophagus stoma button of a tenth embodiment of the invention.

When the shaft portion (1) of the esophagus stoma button of the invention is allowed to always stay in a body and it is necessary to provide its body portion with a fixing section, it is preferable that the shaft part (1) catches on a stomach cardia. A balloon which closes the entire cardia is not preferable because the balloon hinders the passage of saliva or contents obtained through a mouth by means of swallow training. Thereupon, in the present invention as shown in FIG. 18, the tip end of the shaft portion (1) is of a Malecot type structure (30). This structure is preferable because the entire cardia is not closed. A shape, a structure and a material thereof are not especially limited, but in order to maintain the shape in a stomach for a long term, a structure in which a shape memory alloy is embedded in the Malecot section is preferable.

Figure 8:
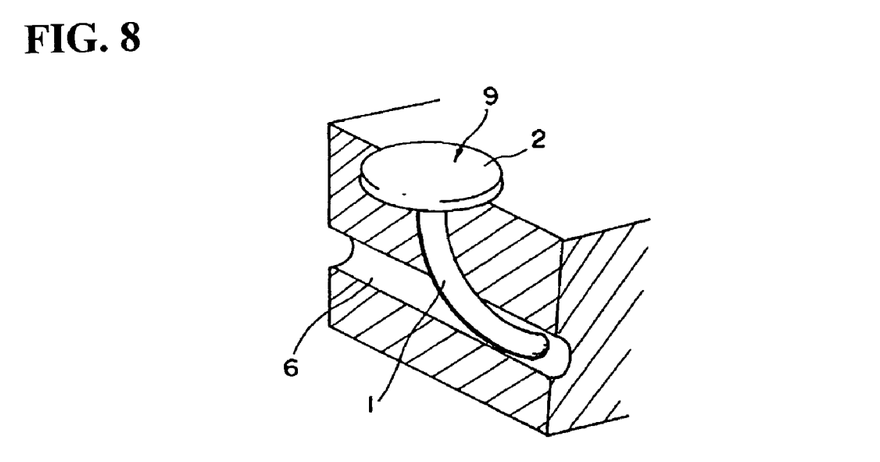
FIG. 8 is a schematic view showing the esophagus stoma button and its indwelling state in the first embodiment of the invention.
Figure 10:
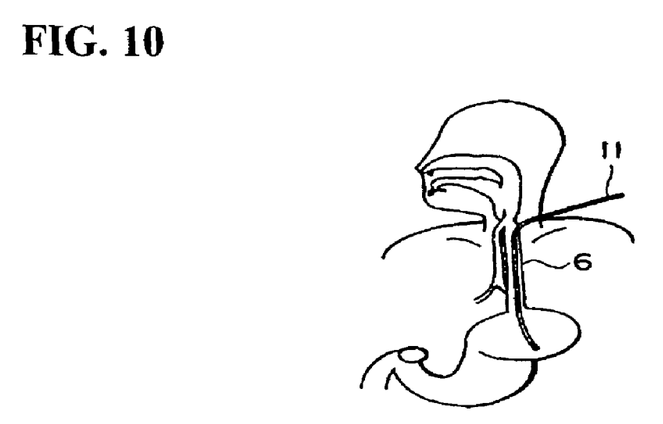
FIG. 10 is a schematic view showing a first example for inserting the esophagus stoma button of the invention.

Next, a using method of the esophagus stoma button of the present invention will be explained using the drawings. According to the esophagus stoma button of the first embodiment as one example, as shown in FIG. 10, a route extending to the esophagus (6) from outside of body is secured first, and a stay-tube (11) is inserted for discharging bodily fluid or infusing chemical liquid or eutrophic. After a fistula is completed, the esophagus stoma button (9) of the present invention is inserted along the stoma such that its tip (tip of the shaft portion (1)) is directed toward an anus, and the flange portion (2) is fixed by means of a tape or the like. With this operation, as shown in FIG. 8, since a portion (flange portion (2)) projecting from body surface is flat and extremely small, even if the esophagus stoma button (9) is allowed to stay in the body for a long term, it is possible to largely reduce the burden on a patient, and it is possible to largely reduce the adverse possibility that the patient himself or herself intentionally pulls out the tube. When bodily fluid is to be discharged or chemical liquid or eutrophic is to be infused, the esophagus stoma button (9) is pulled out, the stay-tube (11) is inserted from the stoma, its tip is allowed to stay at a desired position and then, a predetermined procedure is carried out. After the predetermined procedure is completed, the stay-tube (11) is pulled out, and the esophagus stoma button (9) is allowed to stay in the body again as described above.

Figure 11:
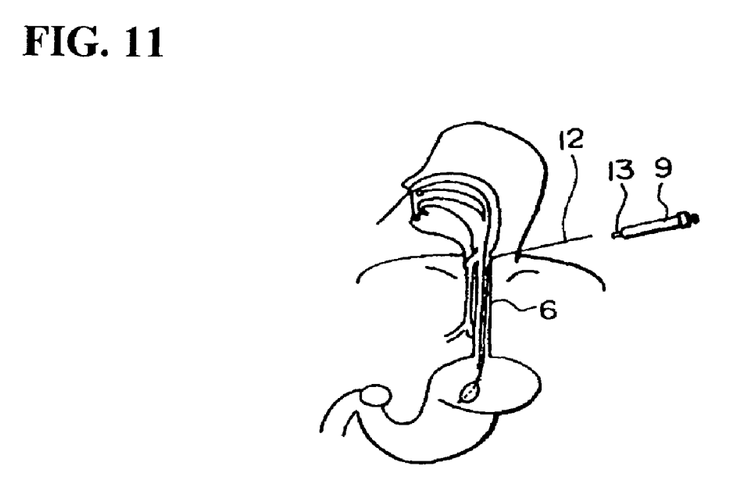
FIG. 11 is a schematic view showing a second example for inserting the esophagus stoma button of the invention.

When an esophagus stoma button (9) having a lumen (1a) of the second embodiment of the present invention shown in FIG. 2 is used, a route extending to the esophagus (6) from outside of body is secured and at the same time, the esophagus stoma button (9) of the invention is allowed to stay in the stoma such that its tip is directed an anus. That is, as shown in FIG. 11 for example, a dilator (13) into which the esophagus stoma-button (9) is previously fitted is inserted into a route formed in the esophagus (6) from the outside of the body along a guide wire (12) and then, the guide wire (12) and the dilator (13) are pulled out, and the esophagus stoma button (9) is allowed to stay in the body. Alternatively, the esophagus stoma button (9) is inserted into a sheath tube which is capable of being divided in the longitudinal direction and which is allowed to stay in a route formed in the esophagus from the outside of the body and then, the sheath tube is pulled out while dividing the same, and the esophagus stoma button (9) is allowed to stay in the body. Alternatively, the esophagus stoma button (9) may be allowed to stay in the body by a combination of the above-described two ways. Then, the esophagus stoma button (9) is fixed by a medial tape, a fixing band or one needle suture.

Figure 9:
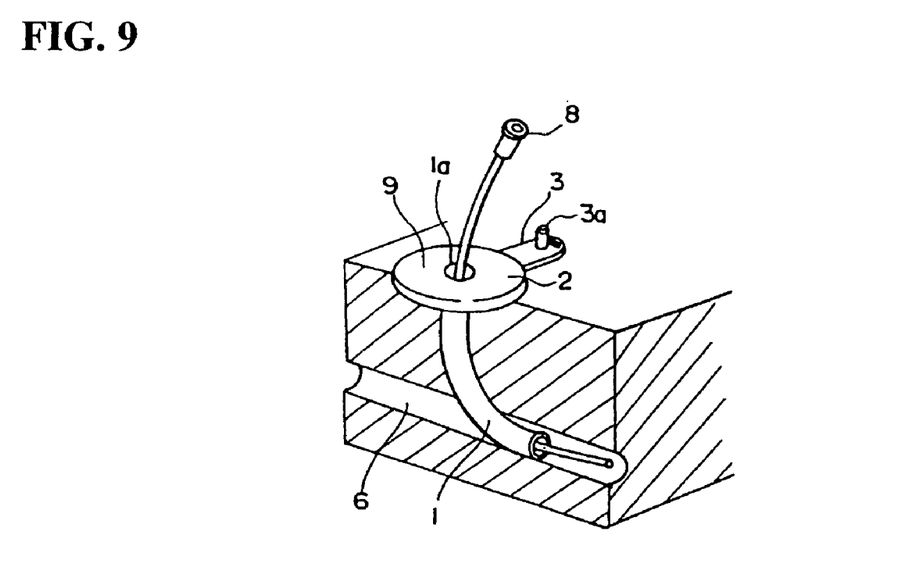
FIG. 9 is a schematic view showing the esophagus stoma button and its indwelling state in the second embodiment of the invention.

According to the esophagus stoma button of the second embodiment of the present invention, as shown in FIG. 9, since the shaft part (1) is of cylindrical, the tube (8) for discharging bodily fluid or infusing chemical liquid or eutrophic can freely be inserted and pulled out before the stoma is completed. Thus, when procedure is not required, the tube (8) can be pulled out. In that case, since the projecting portion from the body is flat and small, it is possible to free a patient from inconvenience of the tube projecting outside from the body from an initial stage of the procedure. When procedure such as discharging of bodily fluid or infusion of chemical liquid or eutrophic is not carried out, a plug (3a) of the cap portion (3) provided on the flange part (2) is inserted into the opening of the lumen (1a) of the shaft portion (1), and contents are prevented from leaking from the body. Since the cap portion (3) is connected to the flange part (2), there is no adverse possibility that the cap portion (3) is lost when it is not required. Since the check valve (4) is provided in the vicinity of the flange part (2), it is possible to reliably prevent the contents from leaking out from the body, and it is possible to avoid inconvenience of patient or a tender such as contamination caused by the leakage.

When the tip of the shaft part (1) is allowed to stay in a stomach (or intestine) also as shown in FIG. 12, the esophagus stoma button (9) of the present invention is inserted in the above-described method, but especially when the esophagus stoma button (9) is allowed to stay in the intestine, after the shaft part (1) of the esophagus stoma button is inserted up to the stomach, the guide wire is inserted to a portion of the shaft part (1) closer to its tip in the esophagus stoma button (9), the weight (28) is inserted into a pylorus of the stomach while turning the patient and then, the shaft part (1) is pushed toward the anus together with the guide wire or fluid is infused into the balloon (29) to expand the same, and the shaft is pushed toward the anus by peristalsis of the intestine. When the esophagus stoma button is to be replaced after a stoma is completed, if the esophagus stoma button is to be inserted into a stomach and the shaft part (1) is soft, after the esophagus stoma button is inserted in a state in which the button is integral with the stylet (17), the soft tube can be allowed to stay in a body by pulling out only the stylet (17), and a burden can be eliminated from a living body. When eutrophic is to be infused, if the transfusion tube is connected and fixed to the flange part (2), the procedure can reliably be carried out. After the procedure is completed, the transfusion tube is detached, and the cap portion (3) is attached. With this operation, leakage can be prevented. If the shape of the cap portion (3) is curved surface shape which is not catchy, the cap is not detached unintentionally. Thus, when the tip of the shaft part (1) is located in a stomach (or intestine), it is unnecessary to insert or pull out the tube for discharging bodily fluid or infusing chemical liquid or eutrophic whenever such procedure becomes necessary. Thus, trouble of a patient or a tender can largely be reduced. If the patient repeats the pulling-out action of the tube by himself or herself, the tube is fixed at the cardia by allowing the tube to stay in the body such that the Malecot type structure (30) of the shaft is located at the cardia, and it is possible to prevent the esophagus stoma button of the present invention from being pulled out.

INDUSTRIAL APPLICABILITY

According to the present invention as described above, when procedure such as discharging of bodily fluid or infusion of chemical liquid or eutrophic is carried out through a route formed in an esophagus, a tube can be pulled out or it is unnecessary to pull out the tube when such procedure is not carried out. A portion of the esophagus stoma button which stays in a body instead of the tube and which projects from the body is extremely small. Therefore, even if the esophagus stoma button is allowed to stay in the body for a long term, a burden on a patient can largely be reduced, and the adverse possibility that the esophagus stoma button is intentionally pulled out by the patient can also be reduced largely.

The invention claimed is:

1. An esophagus stoma button, comprising:
   a shaft;
   the shaft having a rear end with an opening and another end with a rounded tip;
   a flange at the rear end of the shaft; wherein said shaft part provided at its rear end with a movable connector having a convex sphere: said flange provided with a holder located between said movable connector and said flange: wherein said holder having a concave sphere so that the shaft part and the flange held by each other and movable in any direction;
   a lumen having a generally circular cross section in an area ranging from the shaft to the flange;
   a means for fixing a catheter for transfusion in the flange with a flat and generally circular shape; and
   a cap having a top and a bottom, the cap integrally formed on the flange by a belt, for tightly closing the opening, the bottom having a plug fitting into the lumen, and the top having a substantially domical shape so that when the plug is fitted into the lumen, the top defines an exposed external surface so that a finger or nail can not easily catch.

2. The esophagus stoma button according to claim 1, further comprising
   an attachable and detachable metal wire in the area ranging from the opening of the flange to the vicinity of the tip of the shaft.

3. The esophagus stoma button according to claim 1, further comprising
   a movable connector at the rear end of the shaft and a holder for the movable connector, wherein the shaft and the flange can be held by each other at a plurality of angles.

4. The esophagus stoma button according to claim 3, wherein the movable connector comprises a sphere held with the holder.

5. The esophagus stoma button according to claim 1, further comprising
a plurality of weights with a spherical shape made of metal or ceramic,
or a spherical or cylindrical weight having a small hole penetrating a central part of the weight, at the tip of the shaft.

6. The esophagus stoma button according to claim 1, further comprising
an expandable and shrinkable balloon at the outer side of the shaft;
a lumen ranging to the balloon in the shaft;
a means for tightly closing fluid infused into the balloon ranging to the lumen; and
a means for connecting an attachable and detachable tool to infuse the fluid in the flange.

7. The esophagus stoma button according to claim 1, wherein the tip end of the shaft is of a Malecot type structure.

8. An esophagus stoma button according to claim 1, further comprising
a check valve in the vicinity of the opening of the flange.

9. The esophagus stoma button according to claim 8, further comprising
an attachable and detachable metal wire in an area ranging from the opening of the flange to the vicinity of the tip of the shaft.

10. The esophagus stoma button according to claim 8, further comprising
a movable connector at the rear end of the shaft and a holder for the movable connector,
wherein the shaft and the flange can be held by each other at a plurality of angles.

11. The esophagus stoma button according to claim 10, wherein the movable connector comprises a sphere held with the holder.

12. The esophagus stoma button according to claim 8, further comprising
a plurality of weights with a spherical shape made of metal or ceramic,
or a spherical or cylindrical weight having a small hole penetrating a central part of the weight at the tip of the shaft.

13. The esophagus stoma button according to claim 8, further comprising
an expandable and shrinkable balloon at the outer side of the shaft;
a lumen ranging to the balloon in the shaft;
a means for tightly closing fluid infused into the balloon ranging to the lumen; and
a means for connecting an attachable and detachable tool to infuse the fluid in the flange.

14. The esophagus stoma button according to claim 8, wherein the top end of the shaft is of a Malecot type structure.

15. The esophagus stoma button according to claim 1, wherein the cap portion has a curved surface.

16. An esophagus stoma button, comprising:
a shaft;
the shaft having a rear end with an opening and another end with a rounded tip;
a flange at the rear end of the shaft; wherein said shaft part provided at its rear end with a movable connector having a convex sphere; said flange provided with a holder located between said movable connector and said flange;
wherein said holder having a concave sphere so that the shaft part and the flange held by each other and movable in any direction;
a lumen having a generally circular cross section in an area ranging from the shaft to the flange;
a means for fixing a catheter for transfusion in the flange with a flat and generally circular shape; and
a cap having a top and a bottom, the cap, integrally formed on the flange, for tightly closing the opening, the bottom having a plug fitting into the lumen, and the top having a substantially domical shape so that when the plug is fitted into the lumen, the top defines an exposed external surface such that the belt does not extend beyond an outer circumference of the flange.

* * * * *